United States Patent [19]

Vance

[11] 4,295,133
[45] * Oct. 13, 1981

[54] APPARATUS TO INDICATE WHEN A PATIENT HAS EVACUATED A BED OR DEMONSTRATES A RESTLESS CONDITION

[76] Inventor: Dwight A. Vance, 8709 E. 29th, Tulsa, Okla. 74129

[*] Notice: The portion of the term of this patent subsequent to Dec. 18, 1996, has been disclaimed.

[21] Appl. No.: 949,969

[22] Filed: Oct. 10, 1978

Related U.S. Application Data

[63] Continuation-in-part of Ser. No. 794,041, May 5, 1977.

[51] Int. Cl.³ .............................................. G08B 21/00
[52] U.S. Cl. .................................. 340/573; 340/575; 340/636; 340/666; 340/667
[58] Field of Search ............... 340/573, 575, 666, 667, 340/568, 636; 331/DIG. 3, 108 D

[56] References Cited

U.S. PATENT DOCUMENTS

| | | | |
|---|---|---|---|
| Re. 28,754 | 3/1976 | Cook et al. | 340/666 |
| 3,594,751 | 7/1971 | Ogden et al. | 340/636 |
| 3,982,238 | 9/1976 | Byers | 340/573 |

OTHER PUBLICATIONS

*Electronic Engineer*, May, 1970, p. 55, Fig. 10.
Dean, J. A. et al., "Astable and Monostable Oscillators Using RCA COS/MOS Digital Integrated Circuits", *Digital Integrated Circuits*, RCA, 1971.

*Primary Examiner*—Glen R. Swann, III
*Attorney, Agent, or Firm*—Head & Johnson

[57] ABSTRACT

A switch placed in a bed under a patient comprises two spaced parallel strips of insulating material carrying contact means therebetween. When the strips are straight the switch is closed, and when the strips are bent into an arc the switch is open. The closing of the switch starts an electrical oscillator, which activates a counter, and at a selected count a latch is set to actuate an alarm.

11 Claims, 8 Drawing Figures

Fig. 8

APPARATUS TO INDICATE WHEN A PATIENT HAS EVACUATED A BED OR DEMONSTRATES A RESTLESS CONDITION

CROSS-REFERENCE TO RELATED APPLICATION

This application is a continuation-in-part of the copending application of the same Applicant, Ser. No. 794,041, filed May 5, 1977, entitled: "Apparatus to Indicate When a Patient Has Evacuated a Bed or Demonstrates a Restless Condition".

BACKGROUND OF THE INVENTION

1. Field of the Invention

This invention lies in the field of hospital instrumentation. More particularly, it lies in the field of monitoring the presence and condition of a patient in a bed. Still more particularly, it concerns the monitoring of a patient so as to provide indication of the frequency of movement of the patient, that is, when the restlessness of the patient is greater than normal. This provides a means for determining when the restlessness exceeds a selected amount.

2. Description of the Prior Art

In the prior art, instruments have been provided which monitor the presence, or absence, of a patient in a bed. While this is useful information, it does not serve completely the needs of a hospital. It has been found that patients often have bed falls when they try to leave a bed, and it is important to provide indication to the nursing staff that the patient is in a restless mood and may be trying to get out of the bed. It is important to recognize this condition so as to avoid the final step of getting out of bed and falling. This instrument is designed to provide an advance indication of a possible bed fall.

SUMMARY OF THE INVENTION

It is a primary object of this invention to provide a monitoring instrument whereby the nursing staff can have indication that a patient is in bed and is restless beyond a selected condition, and also to have an indication if the patient is, or has been, out of bed.

These and other objects and the limitations of the prior art are overcome in this invention by providing a switch means which is placed in the bed between the mattress and the spring, under the hips of the patient, so that under the weight of the body, switch contacts can be opened or closed selectively.

A signal processing means is connected to the contacts in the switch means and is responsive to a first signal when the patient is in the bed, and a second signal when the patient is not in the bed. Means are provided for charging a capacitor at a controllable selected rate when the second signal is received, and for discharging the capacitor at a selected rate when the first signal is received. In other words, when the patient is out of the bed, the capacitor is charged; and when the patient is in the bed, the capacitor is discharged. However, since the patient is never completely at rest in the bed, there will be occasional interruptions and exchanges of these signals, caused by the tossing and turning of the patient, so that the contacts will close and open responsive to each of the turnings, etc. Normal patients toss and turn in their sleep at widely spaced intervals. On the other hand, patients who are restless and moving about, will cause a more frequent closing and opening of the contacts.

This invention is designed to be able to detect the difference in frequency and effective duration of opening and closing of the contacts, corresponding to restlessness as compared to normal movement of the patient.

If the patient is out of the bed, then the capacitor charges and quickly reaches a selected maximum voltage E; and when this voltage is reached, a latch is set which disables the discharging mechanism so that the capacitor remains charged and the latch remains set until it is reset manually. When a latch is set, a signal is sent to the nurses' station.

When the rate of change of the contacts is frequent, the capacitor does not have an opportunity to fully discharge during the time that the first signal is present, and consequently, charge continues to build up on the capacitor and its voltage continues to rise over a period of time, which can be selected by adjustment of the rates of charge and discharge of the capacitor. In other words, the rates of discharge and charge of the capacitor can be set so that the latch will operate after a selected time when the frequency is higher than a selected number, indicating the degree of restlessness which is to be detected by the instrument. For rates of movement of lower frequency, the capacitor never reaches the selected voltage E, and the latch is not set, indicating that there is low possibility of the patient being restless enough to attempt to leave the bed.

Means are provided for transmitting to the nurses' station the fact that the latch is set, and also if desired, to transmit a signal indicative of the frequency of the restless movement of the patient.

In a second embodiment, switch means are provided for determining when the patient is out of bed. Then, after a selected time delay, a latch is set and alarm sounds. Part of this apparatus includes means for setting a latch and alarm when the battery supply for the system drops below a selected minimum. Once this happens the latch cannot be reset unless the battery is replaced or the equipment turned off.

BRIEF DESCRIPTION OF THE DRAWINGS

These and other objects and advantages of the invention and a better understanding of the principles and details of the invention will be evident from the following description taken in conjunction with the appended drawings in which.

DESCRIPTION OF THE PREFERRED EMBODIMENT

Figure 1:
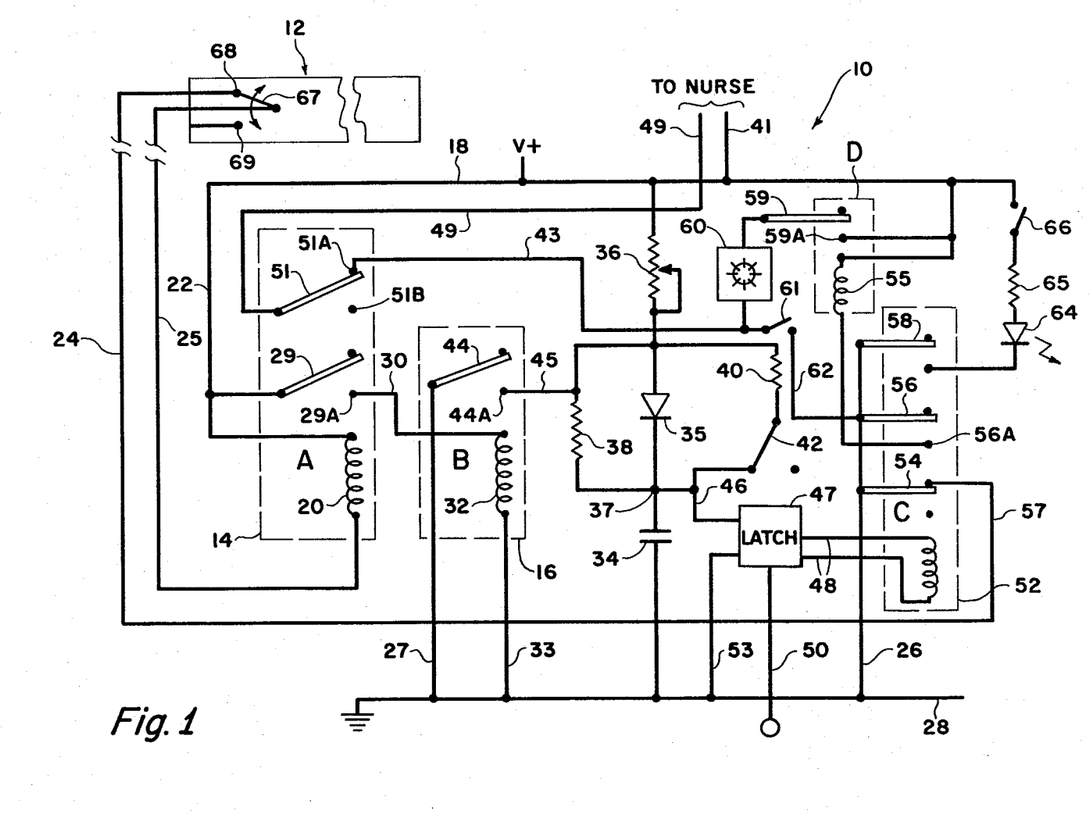
FIG. 1 indicates one embodiment of the circuit diagram of the signal processing unit.

Referring now to the drawings and in particular to FIG. 1, there is shown a circuit diagram of one embodiment of this invention. Indicated generally by the numeral 10 is the signal processing means, and by numeral 12, the switch means or the binary signal generating means.

A switch means 12 is an assembly adapted to be placed in the bed under the patient and responsive to the weight of the patient, to cause a contact 67 to move to or from one contact 68 to or from another contact 69. Thus, there is a circuit closing (or opening) between the two conductors 24, 25 connected to the switch. One of the conductors 24 goes to a relay contact 54 and by lead 26 to ground 28. The other lead 25 goes to a relay coil 20 of the relay 14. The other end of the relay coil goes by lead 22 to a line 18 which has a plug voltage V. When the contact 54 is closed and the contact 68 is closed, then the relay 14, indicated by the dashed line 14, will pull in, and the moveable contacts 29 and 51 will move down to the "on" contacts.

Contact 29 is connected to lead 22 and to the voltage V. A corresponding contact 29A of relay 14 goes to the coil 32 of another relay 16, the second end of the relay coil 32 going by lead 33 to ground. Consequently, when relay 14 pulls in contact 29, contact 29A carries the plus voltage V to the coil 32 of the second relay 16 and causes it to pull in the moveable contact 44 to the fixed contact 44A, to connect via lead 45 and resistor 38 to one lead 37 of a capacitor 34, the other terminal of which is connected to ground 28.

The capacitor 34 is charged by means of a rectifier 35 through a variable resistor 36 connected to the voltage V. Thus normally the capacitor is charged at a selected rate determined by the resistor 36, through the rectifier 35. However, whenever relay 16 pulls in, the terminal 37 of the capacitor is connected through resistor 38, line 45 contacts 44 and lead 27 to ground, and the condenser then discharges at a rate corresponding to the resistance 38.

There is a second resistor 40 which may be fixed or variable, that is, connected at one terminal by means of a manual switch 42 to the terminal 37 of the capacitor 34, and at its other terminal through lead 45 to the moveable contact 44 of relay 16 to ground. Thus when the switch 42 is in the position shown, a considerably different value of discharge resistance 40 as compared to 38 can be utilized so as to radically change the rate at which the condenser discharges. The purpose of these resistors will be discussed in connection with FIG. 2.

When the contacts 67 and 68 are closed, relays 14 and 16 are pulled in, and the capacitor is discharged. When the contact 67 moves to 69, the circuit between leads 24 and 25 is broken, and the relays are open, and the capacitor 34 begins to charge through the resistor 36. If there is no further movement of the contact 67 in the switch means 12, the voltage of the capacitor will rise on an exponential curve; and when it reaches a selected value E, it will close a latch 47 through lead 46, the latch being connected through lead 53 to ground. When the latch 47 closes, a relay 52 is closed. The latch 47 can be opened by resetting the latch by appropriate potential applied to lead 50 to the reset terminal of the latch, as is well-known in the art.

One of the contacts 54 of the relay 52 is connected to ground through lead 26, and the other contact through 57 to leads 24 and 25 and switch contact 67 to the relay 14. When the latch is pulled in, the contact 54 breaks the circuit so that thereafter so long as the latch is on relays 14 and 16 cannot be closed, and, consequently, the capacitor 34 is not discharged, and the latch stays on.

A second moveable contact 56 is connected to ground through lead 26 and closes to terminal 56A which connects one end of the coil 55 to ground, the other end being connected to the voltage V so that relay 58 pulls in contact 59 and places high voltage on the signal device 60 which may be a light, or a buzzer, or equivalent device, provided the manual switch 61, which is connected through lead 62 to ground 28, is closed. Thus, when the latch 47 closes, relays 14 and 16 are locked open, and the signal device 60 is enabled so that if the switch 61 is closed, an appropriate signal will be set. Means are provided to transmit this fact that the latch is closed by means of lead 43 from the switch 61, through contacts 51 and 51A of relay 14, and then to the nurses' station by lead 49 and back by lead 41 to the voltage V. Thus, a signal light at the bed and at the nurses' station can be provided.

If desired, another contact 58 on the relay 52 can be used to close the circit to ground an indicating diode (LED) 64 through resistance and manual switch 66 to the voltage V.

Figure 2:
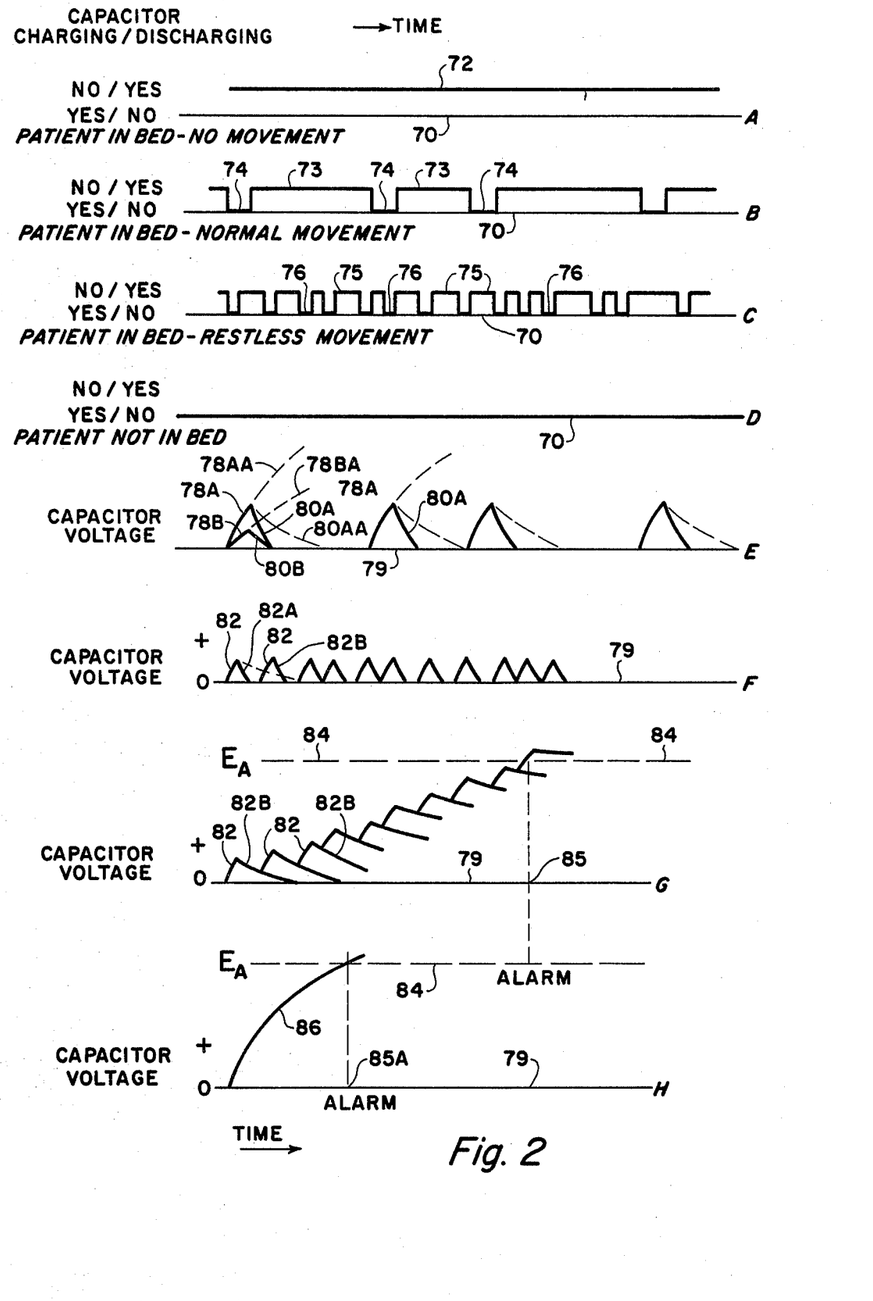
FIG. 2 illustrates the type of signals at various points in the diagram of FIG. 1.

Referring now to FIG. 2, there are eight separate sections A, B, C, . . . H, which indicate various circuit conditions in the monitoring unit signal processing means. In section A of FIG. 2, there is shown a base line 70 and a parallel line 72 which indicates that a signal is present which indicates that a patient is in bed and there is no movement. The line 72, representing voltage of current, is constant.

It is obvious from the circuit diagram of FIG. 1, that the lead 24 can be connected either to terminal 68 or 69, so that a normally open or normally closed switch contact 67 can be provided. While the circuit diagram of FIG. 1 is drawn for a particular switch condition 67, it will be obvious that a corresponding diagram can be drawn using the same relays, etc. for the opposite connection of the switch contact 68 and 69. FIG. 2A indicates the current situation for FIG. 1 when the patient is in bed and there is no movement.

As the patient moves in a normal movement, that is, occasional turning or lifting his hips and dropping them to change position in the bed, there will be occasional interruptions of the line 72, indicating that when the weight of the body is removed from the switch 12, current 72 will be interrupted, and the current flowing then on leads 24 and 25 will look like FIG. 2B. That is, there will be considerable time period 73 when the current will be constant like 72, and then there will be an interruption for a short period 74. There may be several bounces up and down and then it will be constant again 73 for another period. This would be considered a normal condition for a patient in bed. The more sedated the patient, the fewer the interruptions 74.

Referring momentarily now to FIG. 2E, there is shown a base line 79 and a curved line 78A which is part of an extension curve in dashed outline 78AA. This represents the rise in voltage on the capacitor 34 when there is no discharge and the capacitor is being charged by the resistor 36 and diode 35. In other words, when the current 73 drops, the relays open, and the capacitor charges for a short period of the current 74. Then when the current rises to 73 again, the relays pull in and discharge the capacitor, and the potential of the capacitor drops along the curve 80A. Then later when the next interruption 74 occurs, the voltage will rise again 78A and drop 80A, and so on. Since the current drops to 0 for the base line 79 in between each of the chargings, it is seen that there is no tendency for the voltage to build up beyond a nominal small value which immediately is discharged from the capacitor.

Referring now to FIG. 2C, there is a condition where the patient is far more restless than in FIG. 2B, indicating a much more frequent change from a condition 75 to another condition 76, and back to 75. In other words, if every few minutes the patient is turning or tossing, the current flow 75 which corresponds to that of 73 will drop to 0, and then back again for short periods. When this happens (referring to FIG. 2F), there will be more frequent chargings 82 and dischargings 82A. But again, if the rates of charge and discharge are set to one mode of operation, the capacitor voltage drops substantially to 0 each time the condition happens.

Returning now to FIG. 2E and to FIG. 1, there is seen in FIG. 1 that a manual switch 42 permits the inclusion of a discharge resistor 40 which can be low in resistance which means rapid discharge, or when that switch is opened, the resistor 38 which is the high resistor will cause a slow and long, drawn-out discharge which would be represented in FIG. 2E by the discharge curve 80AA. In other words, when the slow discharge takes place as shown in FIG. 2G, the discharge 82B is still in progress when the next charging condition 82 occurs and again when it starts to discharge, it does not discharge completely to the base line 79 when it is again further charged, so that there is a continual buildup in voltage of the capacitor until it reaches a value E, shown by the dashed line 84. When capacitor voltage reaches the voltage E as indicated by the dashed line 84, the latch 47 will pull in and cause the relay 52 to pull in, which causes the alarm to be sounded that either the patient has left the bed or that the patient is so restless that he is likely to leave the bed.

Returning now to FIG. 2D, there is shown a base line 70 but there is no current or voltage according to the line 72 of FIG. 2A. This means that the condition in the bed is such that the patient is not in bed. When that condition happens, the capacitor voltage rises along the line 86, FIG. 2H, determined by the charging rate until it equals the voltage E and the alarm is set at a time 85A. This is generally a shorter time than 85 of FIG. 2G when the patient is in bed, but restless.

Older instruments of this sort have indicated the conditions represented by FIGS. 2A and 2D, that is, where the patient is either in bed or is out of bed. However, that is not sufficient in present-day operation. Since it has been found that patients very often will become extremely restless just prior to trying to get out of bed and perhaps have a bed fall, it is necessary to be able to recognize the condition of restlessness indicated by FIGS. 2C and 2G, and this is accomplished by adjusting the rates of charge and discharge of the capacitor such that the rate of charge is high and the rate of discharge is low so that the charge will accumulate between successive closings and openings of the switch 12. Therefore, in an appreciable time (say 30-60 minutes), the voltage on the capacitor will build up to the voltage E which causes the latch to operate.

In other words, referring again to FIG. 1, the variable resistor 36 which controls the rate of charge, the fixed resistor 38 which controls the lowest rate of discharge, and the switchable fixed resistor 40, which controls a higher rate of discharge, provide the opportunity to separate in the indication of the instrument the conditions of FIGS. 2B and 2E.

The switch 42 is really a night operation switch and in the daytime where the nurses are in and out of the patient's room frequently and the switch 42 is generally closed which causes a rapid discharge and a condition of discharge like 82A in FIG. 2F, so that there is no signal unless the patient is actually leaving the bed.

In FIG. 1, the connection of relay contacts 51 and 51A and leads 49 and 41 of the nurses' station when the latch is off provides indication of the off-and-on nature of the trace of FIG. 2C. As a relay 14 operates and relay contact 51 opens and closes the circuit, the light in the nurses' office indicates the on-off nature of the trace of FIG. 2C. Then when the latch is set and the relay 14 is disabled, the light will remain on continuously, just as the signal 60 will remain on continuously until the latch is reset by appropriate voltage applied to lead 50, as is well known in the art.

While there are many embodiments of a switch means such as indicated by numeral 12 in FIG. 1 that can be used with a signal processing circuit of FIG. 1, there is a particular design that has been proved to be very effective and is completely responsive to the action of the patient.

Figure 4:
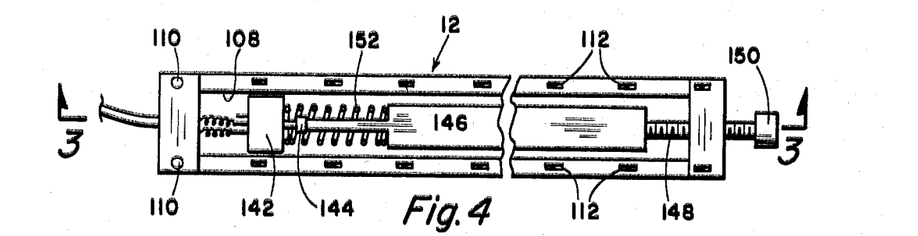
Figure 5:
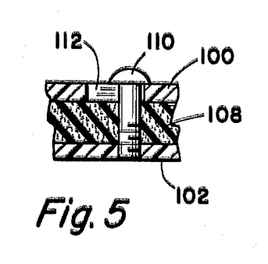
Figure 6:
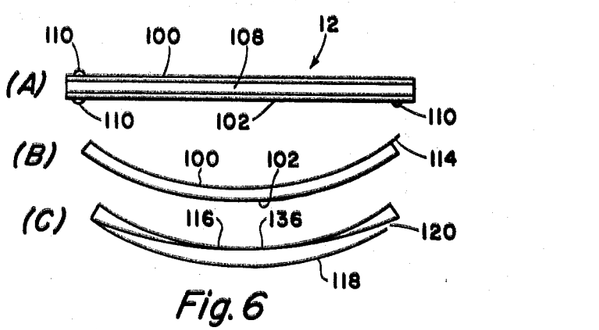

Several embodiments of such a device are indicated in FIGS. 3, 4, 5, 6, and 7. One embodiment includes a first strip of flexible insulating material 100 of a long, narrow shape and a second strip 102 of a similar shape. These are clamped together by screws 110 to a block 104 at one end. There are two narrow strips of corresponding insulating material 108 on each edge of the strips shown in FIGS. 3 and 4 which keep the two strips separated. They are held together by screws 110 shown in FIG. 5, which operate through slots 112 in the top strip. The reason for this is shown in FIG. 6 where, in FIG. 6A, the straight linear condition of the device, the upper and lower strips are of equal length and are spaced apart by the insulating spacers 108. However, when the strips are bent into an arc as shown in FIG. 6B, it will be seen that the top strip is then extended 114 beyond the end of the device. This is the reason for the slots 11, to permit the top strip to slide with respect to the bottom strip. It has been found desirable to use a somewhat compressible material 108 so as to avoid the necessity of slots in the material 108.

Near the end 104 of this device 12 is a switch 142 which has two or three leads as indicated in FIG. 1, which are attached to a cord 101 which comprises the leads 24 and 25 of FIG. 1. In between the two strips 100 and 102, there is a third strip 146, generally of the same material as the top and bottom strips. It is sufficiently rigid such that when guided by the top and bottom strips it can be pushed at the end opposite to 104 and will move against the push button 144 of the switch 142. The block 106 is locked to the bottom strip 102 by screw 110, and there is a threaded opening in which a screw 148 having a knurled head 150 can be turned. As shown in FIG. 4, which is a top view, the pusher 146 is narrowed for a portion of its length, and a spring 152 is provided which tends to keep the pusher 146 tight against the screw 148 and away from the push button 144.

When this device is placed on top of the spring and under the mattress at about the hip position of the patient, the weight of the patient on the springs will cause the device to form in an arc as shown in FIG. 6B, with the slippage of the top strip 100. The effect will be to push the pusher strip 146 against the push button 144 and cause a switch 142 to operate.

In normal operation, the device is set in place. When the patient is in position, the knurled knob 150 is turned, pushing the strip against the push button until the signal light shows that contact is made. Then if the patient should lift his weight off of the device, the switch will open; and when his weight falls back onto it again, it will close, and so on.

Figure 3:
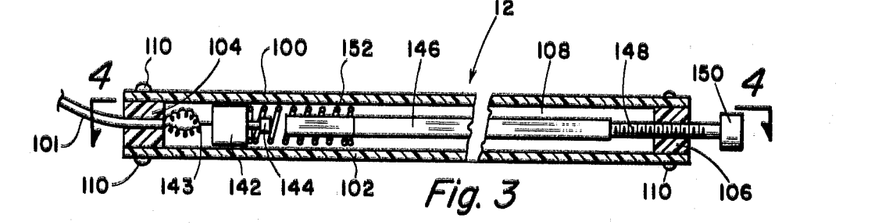
FIGS. 3, 4, 5, 6, and 7 indicate various embodiments and details of the binary signal generating means or switch means which is responsive to the weight of the patient in the bed.
Figure 7:
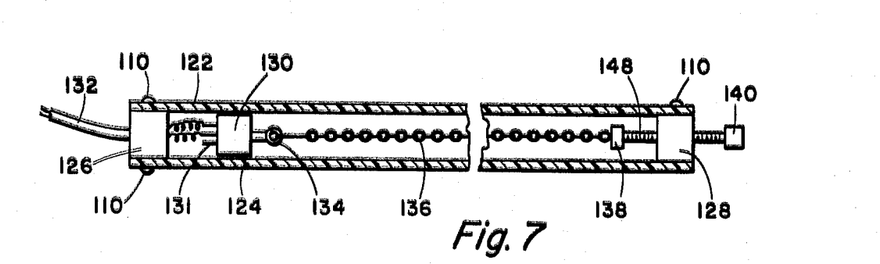

In FIG. 7, there is shown a variation of this design which is similar to that of FIGS. 3 and 4 except that in this case the top strip is fastened to the blocks 126 and 128 at each end. The switch is also fastened to the top strip 122, and the bottom strip 124 operates with slots as shown in FIG. 5. It will be clear from FIG. 6C that when this is formed into an arc, the length of the tensile member 136 will tend to increase and to pull on the ring 134 of the switch 130 to cause the switch to operate. The precise positioning of the tensile member, which might be a simple chain 136, is adjusted by means of a screw 148 with a knurled head 140 and a swivel at 138. Thus, the device can be made in one embodiment of FIGS. 3 and 4 to push on the switch or in an embodiment of FIG. 7 to pull on the switch when the device is bent into an arc. Also, the switches 142 and 130 can be made to open or close the switch as desired and to suit the type or control of FIG. 1, or other variations of this design.

In summary, this device comprises a switch means for closing and opening a switch when a patient is in, or is out of bed and to show by the frequency of closings and openings that the patient is of normal restlessness or of excessive restlessness. By means of a capacitor charging and discharging circuit, of variable rates of charge and discharge and various time constants, a proper selection can be made to cause a latch to be pulled in and a signal sounded whenever the rate of circuit opening and closing is of greater frequency than a selected value, which would indicate that the degree of restlessness is abnormal. Thus, this device can indicate excessive restlessness as well as the previously indicated conditions of patient quiet in bed and patient out of bed. This ability to recognize the degree of restlessness permits the prevention of bed falls since it provides a means for detecting the restlessness which generally precedes the falling out of bed of the patient.

The circuit diagram of the invention has been illustrated in its simplest form in terms of a battery, relays, contacts, and capacitor. In this form it is easy to see what happens when a particular switch or relay is closed. It will be clear, however, that this may not be the optimum practical form of the apparatus, particularly because of the battery drain by the relays.

However, there are electronic equivalents of the relays and contacts which are well known in the art. It could be within the capability of a man skilled in the art to develop the circuit diagram of an analog or digital transistor circuit to be the equivalent of this relay circuit and to accomplish the same operations as the relays, etc. However, each practitioner would have a different method of constructing such transistor circuits, and it would not be possible to cover all such possible circuits by claims. Inasmuch as the relay circuits will do the job, it is not necessary, therefore, to illustrate the invention in terms of analog transistor circuits or digital circuits, the invention being fully described in terms of the claims.

It will be clear from the description of FIG. 1 that while the apparatus being utilized is a capacitor that is charged and discharged, another way of expressing this situation is that the quantity of interest is the magnitude of the electrical charge in the capacitor. Since the potential across the capacitor is proportional to the charge and is more easily measured, then another selected quantity of interest is an electrical potential, the potential across the terminals of the capacitor.

Thus, the signal processing means can be described as:

(1) means representative of the magnitude of a selected physical quantity;

(2) means responsive to an abnormal signal when the patient is not in the bed to increase said magnitude of said physical quantity at at least one selected rate;

(3) means responsive to a normal signal when the patient is in the bed to decrease said magnitude of said physical quantity at a selected one of a plurality of rates;

(4) latch means responsive to said magnitude of said physical quantity to set an alarm when said magnitude reaches a selected value.

It will be clear also that in a digital circuit equivalent to that of FIG. 1, the means representative of the magnitude of a selected physical quantity can be an up/down counter, and the magnitude is the count of that up/down counter. The means to increase the magnitude is means to increase the count or means to make the counter count up, and the means to decrease the magnitude comprises means to make the counter count down.

Commercial digital counting devices are available on the market to count electrical pulses, as from a clock. Pulses applied to one control terminal of the counting device will cause the counter to increase its count, or count up, while pulses applied to another terminal will cause the counter to decrease its count, or count down. The relay contacts that control the charge and discharge of the capacitor 34 can be used to control the up/down count of the counter.

By reference to FIG. 1, it will be clear that signal on leads 49, 41 will show whether the relay contact 51 is closed or open and thus whether the relay 14 is open or closed. The rate of change of this signal from open to closed, to open, etc. will be an indication of the restlessness of the patient. Also, if there is no signal for a long period, it indicates that the patient is in the bed but hasn't moved; while if the signal is on for a long time, it would means that the relay 14 is off and the patient is out of bed.

Figure 8:
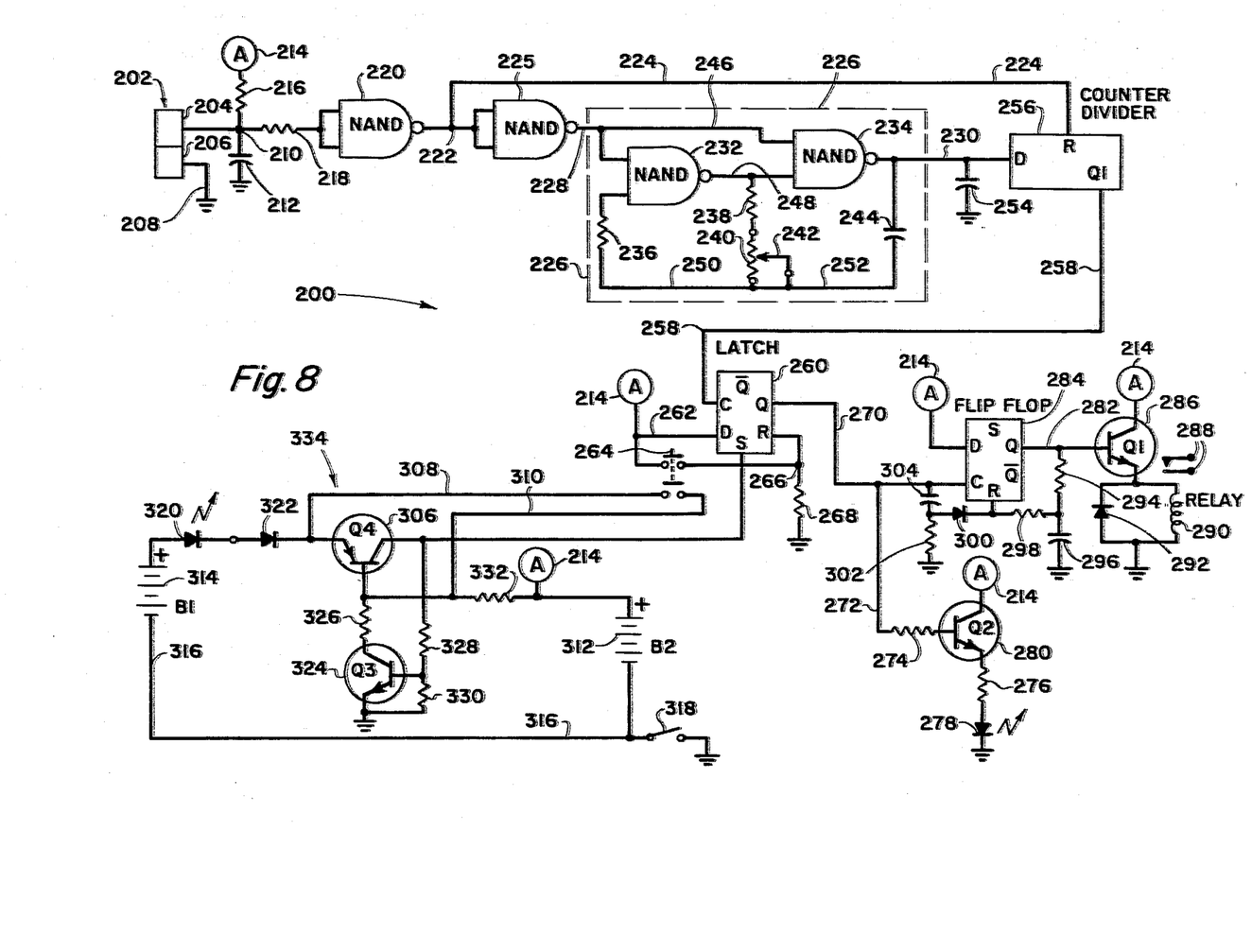
FIG. 8 describes a circuit for monitoring the presence of the patient in bed.

Referring now to FIG. 8, there is shown a second embodiment of this invention indicated generally by the numeral 200. This employs a switch 202 placed in the bed under the patient similar to that identified by numeral 12 of FIG. 1. Preferably, the contacts are normally open when the patient is not in the bed. The weight of the patient causes the contacts to close. These are brought to terminals 204 and 206 of FIG. 8. The voltage of the capacitor 212 measured at the junction 210 is normally high when the contacts are open; and when they are closed, they short circuit the capacitor 212 and the junction voltage 210 drops to zero. This junction is connected through resistor 218 to a NAND gate 220.

When the input to NAND gate 220 is low, the output at 222 is high, and this potential goes by line 224 to the reset terminal R of a counter 256 which is used as a divider or as an adjustable time delay means. This high potential resets the counter and keeps it in a waiting condition until the junction 222 drops to a low potential, and this occurs when the input to the NAND gate 220 is high, when the switch 202 is open. When the switch is open, the capacitor 212 rises to the potential of the battery terminal 214, and the high input to NAND 220 makes the output at 222 low, and the output of the second NAND gate 225 goes high at 228.

The dashed outline 226 represents a standard type of oscillator of adjustable frequency, determined by the value of the capacitor 244 in series with the resistors 240 and 238, which create a feedback around the NAND gate 234. The output of this oscillator 226 goes by lead 230 to the clock input terminal D of the counter 256. Each alternation of the oscillator 226 adds a count to the counter 256. When it reaches a desired number, the terminal Q1 goes high, or positive. This voltage on line 258 goes to the latch 260 at the C terminal. When the C terminal goes high, the Q terminal goes high, and lead 270 leads to resistor 274 and the base of transistor Q2, number 280. When the base of the transistor 280 rises, the transistor carries current, which provides a potential on the light emitting diode 278, which shows a red light as an indication that the latch 260 has been set.

At the same time, the Q output of latch 260 goes to the C terminal of a flip-flop 284, which is set when the C terminal sees a high potential. The high potential on the Q output on line 282 raises the base of the transistor Q1, number 286, and this causes the transistor 286, which is fed by battery potential at 214, to carry a current through the relay coil 290 to ground. The current through the relay pulls in the contacts 288, which can be connected to a second alarm or to a pair of conductors to a nurses signal board, or provide any type of alert signal that is desired. The diode 292 connected across the relay is simply for the purpose of squelching high voltage transients when the relay circuit is broken.

The capacitor 304, resistor 302, and diode 300 are provided as a filter to filter out transients on the C terminal.

The series resistor 294 and capacitor 296 with resistor 298 connected to the reset terminal provide a time delay circuit after the Q terminal goes high. When a sufficiently high voltage appears on the capacitor 296, it controls the reset and turns off the flip-flop. Any selected period, such as two or more seconds delay, can be provided after which the alarm can be turned off. It can also be turned off by means of the manual reset switch 264.

Battery potential 214 is applied through lead 262 to the D terminal of latch 260. Another lead goes through switch 264 to the reset terminal R of the latch 260 which resets it. Thus, when the latch 260 is set by the fact that the switch 202 is open and a suitable time delay has passed, that latch 260 can be reset manually by switch 264.

The battery terminals 214 which, as indicated, are applied at various points in the circuit diagram, are derived from a power supply battery B2 identified by numeral 312. A power switch for the battery is indicated by 318.

The circuit indicated generally by numeral 334 is for the purpose of monitoring the potential of the power battery 312. If this battery drops below a selected potential, the operation of circuits 200 will not, as described, be reliable; and therefore, it is important that when the battery drops below a selected reference voltage, that an alarm be sounded and the battery be replaced or recharged.

The reference battery B1, numeral 314, is tied negative-to-negative with battery 312 by means of lead 316. The positive terminal of battery 314 then goes through a light emitting dioe 320, through a standard diode 322, to a transistor 306 to the set terminal of the latch 260. The positive terminal of battery 312 is connected by resistor 332 to the base of transistor 306. When the positive voltage of 312 drops below that of battery 314 by a selected voltage, transistor 306 will conduct and by the tie-in through resistor 328 between transistors 306 and 324, transistor 324 will conduct. The light from the light emitting diode 320 serves as a signalling light that the voltage of the battery is low.

What has been described is a different and separate type of signal processing circuit, which provides an alarm whenever a patient is out of the bed for a period longer than a selected time interval. Also, a battery voltage monitoring circuit is shown which controls a latch to provide an alarm whenever the battery voltage drops below a selected reference voltage. This battery monitoring circuit can be applied also to the other embodiments of this apparatus.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A monitoring system for a bed patient, comprising:
   (a) a binary signal generating means adapted to indicate one of two possible positions of a body in a bed; and producing a first signal when said body is in a rest position in said bed; and a second signal when said body is out of said bed;
   (b) signal processing means comprising:
   (1) oscillator means actuated responsive to said second signal, said oscillator means comprising;
      (i) a first and a second NAND gate;
      (ii) one input lead from each gate connected to a selected terminal responsive to said second signal;
      (iii) the output of said second gate connected through a capacitor and first resistor to the second input of said first NAND gates;
      (iv) the output of said first NAND gate connected to the second input terminal of said second NAND gate;
      (v) a series second resistor and third resistor connected between the output of said first NAND gate and the junction between said capacitor and said first resistor;
   (2) counter means responsive to said oscillator means;
   (3) latch means responsive to a selected count of said counter means;
   (4) alarm means responsive to the setting of said latch means.

2. The monitoring system as in claim 1 including means to reset said latch.

3. The monitoring system as in claim 1 in which said binary signal generating means comprises a switch means adapted to change from a first operating position to a second operating position responsive to the weight of said body on said signal generating means, in said bed.

4. The monitoring system as in claim 3 in which said switch means comprises;
   (a) a first strip of flexible insulating material;
   (b) a second strip of flexible insulating material;
   (c) insulator spacer means to keep said strips apart and parallel;

said strips and spacer means locked together at one end and adapted to slide, one strip relative to the other when said strips are bent into an arc; and (d) contact means adapted to open and close responsive to the curvature of said switch means.

5. The monitoring system as in claim 4 including substantially rigid insulating strip pusher means responsive to the slippage of one strip with respect to the other to operate said contact means when said switch means is curved.

6. The monitoring system as in claim 4 including tensile means responsive to the slippage of one strip with respect to the other to operate said contacts when said switch means is curved.

7. The monitoring system as in claim 1 including means to transmit to a monitoring station an indication that said latch is set.

8. The monitoring system as in claim 1 including battery means to supply power to said system; and including means to monitor the voltage of said battery means; and means responsive to said monitoring means to set said latch means when said battery voltage is less than a selected value.

9. The monitoring system as in claim 8 in which said means to monitor includes a reference voltage and voltage comparator means.

10. The monitoring system as in claim 9 including means responsive to said monitoring means, when said battery is low, to prevent resetting of said latch means.

11. A monitoring system for a bed patient, comprising:

(a) a binary signal generating means adapted to produce a first signal when a body is in a bed, and a second signal when said body is out of said bed;

(b) oscillator means actuated responsive to said second signal;

(c) counter means responsive to said oscillator means;

(d) latch means responsive to a selected count of said counter means;

(e) alarm means responsive to the setting of said latch means; and wherein (f) said binary signal generating means comprises a switch means adapted to change from a first operating position to a second operating position responsive to the weight of said body on said signal generating means, in said bed; and wherein (g) said switch means comprises;

a first strip of flexible insulating material;

a second strip of flexible insulating material;

insulator spacer means to keep said strips apart and parallel;

said strips and spacer means locked together at one end and adapted to slide, one strip relative to the other when said strips are bent into an arc; and contact means adapted to open and close responsive to the curvature of said switch means.

* * * * *